(12) United States Patent
Parker et al.

(10) Patent No.: US 8,092,988 B1
(45) Date of Patent: Jan. 10, 2012

(54) MEDIUM AND METHOD OF DERIVING AND USING A MUTATED BACTERIA STRAIN

(75) Inventors: Jill E. Parker, Floresville, TX (US); Johnathan L. Kiel, Universal City, TX (US); Homer Gifford, Hardy, AR (US); John L. Alls, Floresville, TX (US); Pedro J. Morales, legal representative, Floresville, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 1264 days.

(21) Appl. No.: 11/820,039

(22) Filed: May 25, 2007

Related U.S. Application Data

(62) Division of application No. 10/828,630, filed on Apr. 9, 2004, now Pat. No. 7,279,320.

(60) Provisional application No. 60/480,280, filed on Jun. 20, 2003.

(51) Int. Cl.
*C12Q 1/00* (2006.01)
*C12N 15/00* (2006.01)

(52) U.S. Cl. .......................................... 435/4; 435/440

(58) Field of Classification Search ........................ None
See application file for complete search history.

(56) References Cited

U.S. PATENT DOCUMENTS

| 5,003,050 A | 3/1991 | Kiel et al. |
| 5,156,971 A | 10/1992 | Kiel et al. |
| 5,902,728 A | 5/1999 | Parker et al. |
| 6,013,520 A | 1/2000 | Parker et al. |

*Primary Examiner* — Albert Navarro
(74) *Attorney, Agent, or Firm* — AFMC Lo/Jazz; Rebecca Greendyke; Paul Heydon

(57) ABSTRACT

A new strain of *Bacillus anthracis* derived from the Sterne vaccine strain of *Bacillus anthracis* by growth on a high-nitrate-concentration, 3-amino-L-tyrosine growth medium.

6 Claims, 5 Drawing Sheets

SEQUENCE LISTING

```
<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide

<400> SEQUENCE: 1
atcaccagag gcaagacacc cccttgtggc                                    30

<210> SEQ ID NO 2
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide

<400> SEQUENCE: 2
tgtaattgga gtagaactga aatcgtcttg                                    30

<210> SEQ ID NO 3
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide

<400> SEQUENCE: 3
gctaactgat tcttgatatt ttgagatgtt                                    30
```

MEDIUM AND METHOD OF DERIVING AND USING A MUTATED BACTERIA STRAIN

CROSS REFERENCE TO RELATED APPLICATION

This application is a division of U.S. patent application Ser. No. 10/828,630, filed Apr. 9, 2004 now U.S. Pat. No. 7,279,320 (hereby incorporated by reference), which claims priority of the filing date of Provisional Application Ser. No. 60/480,280, filed Jun. 20, 2003, the entire contents of which are incorporated by reference.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to the disease of anthrax and, more particularly, to a novel vaccine strain of *Bacillus anthracis*. Anthrax infections are initiated by spores of *Bacillus anthracis*, a gram-positive, rod-shaped bacterium found in soil. *Bacillus anthracis* spores do not divide, have no measurable metabolism and are markedly resistant to biological extremes of heat, cold, pH, desiccation, chemicals and irradiation. In the spore form, *Bacillus anthracis* survives for decades, perhaps centuries. Domestic livestock are frequent victims of the disease, but human cases of anthrax can occur as a result of exposure to infected animals or animal products. Anthrax has also been recognized as a likely biological warfare or terrorist agent.

Anthrax is a complex, poorly understood disease. The pathogenic process of anthrax and the mechanisms of immunity to the disease have not been completely defined. All known anthrax virulence genes are expressed by the vegetative form of *Bacillus anthracis* that results from the germination of spores within the body of the host. Spores introduced into the body by abrasion, inhalation or ingestion are phagocytosed by macrophages and carried to regional lymph nodes. Spores germinate inside the macrophage and become vegetative bacteria. After germination and local multiplication within the macrophage, the vegetative bacteria kill the macrophage and are released into the bloodstream, reaching high numbers (up to $10^8$ organisms per milliliter of blood) and causing massive septicemia. It is believed that no immune response is initiated against vegetative bacilli once they have been released from the macrophage.

It is believed that anthrax bacilli express a range of virulence factors. The two major factors are a tripartite toxin and an antiphagocytic capsule composed of poly-D-glutamic acid. Anthrax toxin and capsule genes are apparently expressed early after germination within the macrophage. The resulting toxemia and bacteremia have systemic effects that lead to the death of the host.

The major virulence factors of *Bacillus anthracis* are encoded on two virulence plasmids, pX01 and pX02. The toxin-bearing plasmid, pX01, is 184.5 kilobase pairs (kbp) in size and codes for the genes (cya, lef, and pagA) that make up the secreted toxins. Regulation of toxin production is also encoded on pX01; it contains transacting regulator genes atxA and atxR.

The three proteins of the toxin are protective antigen (PA), lethal factor (LF) and edema factor (EF). LF is a zinc metalloprotease that inactivates mitogen-activated protein kinase kinase. EF is a calmodulin-dependent adenylate cyclase which causes fluid loss through elevation of cellular cAMP concentrations in affected tissues. Neither LF or EF are toxic alone; they can produce deleterious effects only when combined with PA, so named because of its use in the protective anthrax vaccine. Following the A-B model of toxicity, PA serves as a necessary carrier model for LF and EF and permits penetration into host cells. Lethal toxin, which results from the combination of LF+PA, stimulates the macrophages to release the shock-inducing mediators, necrosis factor $\alpha$ and interleukin-1$\beta$, which are partly responsible for sudden death in systemic anthrax. Edema toxin, which results from the combination of EF+PA, is responsible for the massive edema seen in anthrax. Edema toxin also plays a role in inhibiting phagocytic and oxidative burst activities of polymorphonuclear leukocytes. Bacterial toxins that increase cAMP tend to decrease the immune response of phagocytes, thereby contributing to the development of infection.

The smaller capsule-bearing plasmid, pX02, is 95.3 kbp in size and codes for the genes (capB, capC, capA) involved in the synthesis of the polyglutamyl capsule. pX02 also encodes for a known transacting regulating gene for capsule modulation, acpA. atxA also appears to regulate acpA transcription to some degree.

The capsule is weakly antigenic and antiphagocytic. The toxins are thought to inhibit the immune response mounted against infection while the capsule inhibits phagocytosis of vegetative anthrax bacilli.

In addition to the major virulence factors already described, *Bacillus anthracis* likely expresses other plasmid- and chromosome-encoded genes that contribute to the pathogenisis of the organism. Identification of other genes contributing to virulence is crucial to the further development of effective protection against anthrax.

Expression of the known major virulence factors previously discussed (tripartite toxin and capsule) appears to be regulated by two host-specific cues: elevated temperature and carbon dioxide/bicarbonate concentration. During in vitro growth of *Bacillus anthracis*, synthesis of toxin protein and capsule is greatest when cultures are incubated at elevated (5% or greater) atmospheric $CO_2$ or when bicarbonate is added to culture medium in a closed vessel. Toxin and capsule synthesis is also increased when cultures are incubated at 37° C. compared to when they are incubated at 28° C. $CO_2$/bicarbonate and temperature-controlled gene expression is at the level of transcription. As indicated previously, regulation of the expression of the toxin and capsule genes is mediated by the transcriptional activator atxA; expression of the capsule gene is also controlled by transcriptional regulator acpA.

The effect of these signals ($CO_2$/bicarbonate concentration and temperature) in culture medium may be compared with their physiological role in mammalian hosts; concentrations of $CO_2$ and bicarbonate in humans are similar to those that activate toxin and capsule production in vitro, and the same is true of human body temperature. It is believed that these signals play similar roles in vitro and in vivo by providing an optimal environment for expression of known *Bacillus anthracis* toxin and capsule genes.

As indicated previously, the loss of either plasmid pX01 or pX02 results in a marked reduction of virulence. This forms the basis for effective vaccine production. Historically, vaccine strains of anthrax bacteria were made by rendering virulent strains free of one or both plasmids. Pasteur, a heat-attenuated, pX02-carrying strain is encapsulated but does not express toxin components (pX01−/pX02+). Sterne, an attenuated strain that carries pX01, can synthesize toxin but does not have a capsule (pX01±/pX02−).

It is frequently convenient to class *Bacillus anthracis* with the "*Bacillus cereus* group" of bacilli which on the basis of phenotype comprises *Bacillus cereus, Bacillus anthracis, Bacillus thuringiensis,* and *Bacillus mycoides*. Except for *Bacillus anthracis,* all members of this group are resistant to penicillin. *Bacillus anthracis* is easy to differentiate from other member of the *Bacillus cereus* group by observing the morphological features of the colony on nutrient or blood agar plates. Colonies of most *Bacillus anthracis* isolates have a matt appearance, are fairly flat, markedly tacky, white or grey-white and non-hemolytic on blood agar and often having curly tailing at the edges. The unusually tenacious colonies are able to retain their shape when manipulated; disturbed sections of the colony often stand up like "beaten egg whites." *Bacillus anthracis* is non-motile, sensitive to penicillin and the diagnostic Cherry gamma phage and able to produce the capsule in blood or on nutrient agar containing 0.7% bicarbonate following incubation in a 5-20% $CO_2$ atmosphere.

In practical terms, the demonstration of virulence constitutes the principle point of difference between typical strains of *Bacillus anthracis* and those of other members of the *Bacillus cereus* group. However, there is evidence that the virulence plasmids can be transferred between the *Bacillus cereus* group species through genetic engineering, although it is not clear how stable the resulting hybrids are.

An anthrax vaccine for humans is approved for use in the United States by the Food and Drug Administration. Designated anthrax vaccine adsorbed (AVA), it is an aluminum-hydroxide-precipitated preparation of PA from attenuated, nonencapsulated *Bacillus anthracis* cultures of the Sterne strain. The anthrax vaccination protocol consists of 3 subcutaneous injections given 2 weeks apart followed by 3 additional subcutaneous injections given at 6, 12 and 18 months. Annual booster injections of the vaccine are required to maintain immunity. Mild local reactions consisting of slight tenderness and redness at the injection site can occur in approximately 30% of recipients. Severe local reactions occur infrequently and consist of extensive swelling of the forearm in addition to the local reaction. Systemic reactions characterized by flu-like symptoms occur in fewer than 0.2% of vaccines.

Animal studies have shown that AVA affords protection against inhalational anthrax and a limited trial of a similar vaccine in humans indicated that it afforded considerable protection against cutaneous anthrax. Studies have also demonstrated, however, that the live Sterne spore veterinary vaccine is more protective than the human chemical vaccine. The enhanced protection conferred by the live vaccine probably results from stimulation of the host cellular immune system concurrent with the humoral response to PA. The main limitation of the Sterne vaccine is safety. Its use is sometimes associated with tissue necrosis at the site of inoculation and there have been rare fatalities. Because of these safety concerns, spore vaccines have generally not been used for humans.

The established virulence factors of *Bacillus anthracis* have been the targets of most attempts to develop vaccines. As indicated previously, PA is asserted to be the essential anthrax-derived antigen for the protective action of the current vaccine. Nevertheless, studies have repeatedly demonstrated that titers to PA do not correlate strictly with the level of immunity to anthrax. Moreover, it is important to note that antibodies to PA induced by the vaccine are directed against the action of the toxin and not at the multiplying *Bacillus anthracis* in an infection. It has also been postulated that *Bacillus anthracis* strains could be created by adding foreign genes from other toxic organisms. As indicated previously, studies have shown that virulence plasmids can be transferred between the *Bacillus cereus* group of organisms.

Clearly there is a need for new candidate antigens for vaccine development, especially those that act prior to expression of anthrax toxins into the body. Such vaccines should also be effective against infection with strains that have been engineered with additional toxins.

Critical to development of effective protection against anthrax is an understanding of the initial pathogenesis of the disease and its virulence mechanisms. Events occurring during the initial moments when bacterial pathogens first encounter the host are critical for successful establishment of infectious loci. The pathogenesis of anthrax appears to be related primarily to the unique sensitivity of the macrophage to the activity of lethal toxin, in addition to the adenylate cyclase activity of edema toxin and the antiphagocytic properties of the capsule. As indicated previously, the genes for these virulence factors are induced in response to specific host-related cues, that is, $CO_2$/bicarbonate levels and physiological body temperature. There is a need for a vaccine directed to *Bacillus anthracis* targets vital for early steps in the infection process, containing antigens which elicit antibodies targeted at the spore or germinating cell.

It is therefore a principal object of the present invention to provide a vaccine strain of *Bacillus anthracis* from which may be produced an improved anthrax vaccine which is safe, nonreactogenic, efficacious against genetically engineered strains, and which requires a minimal number of injections to achieve and maintain long-term immunity. It is a further object of the invention to provide a vaccine strain of *Bacillus anthracis* that will enable identification of new genes that contribute to the pathogenesis of the organism and thereby elucidate new antigens that play a role in eliciting a specific, protective immune response early in the infection process.

SUMMARY OF THE INVENTION

In accordance with the foregoing principles and objects of the invention, a new strain of *Bacillus anthracis* is described which is derived from the Sterne vaccine strain of *Bacillus anthracis* by growth on a high-nitrate-concentration, 3-amino-L-tyrosine growth medium. The new strain, designated the *Bacillus anthracis* Alls/Gifford (Curlicue) strain, has a number of unique characteristics that are important in designing a vaccine to restrict the growth of *Bacillus anthracis* in human or animal hosts.

BRIEF DESCRIPTION OF THE DRAWINGS

The invention will be clearly understood from the following detailed description of preferred embodiments thereof read in conjunction with the accompanying drawing wherein.

DETAILED DESCRIPTION OF THE INVENTION

Figure 1:
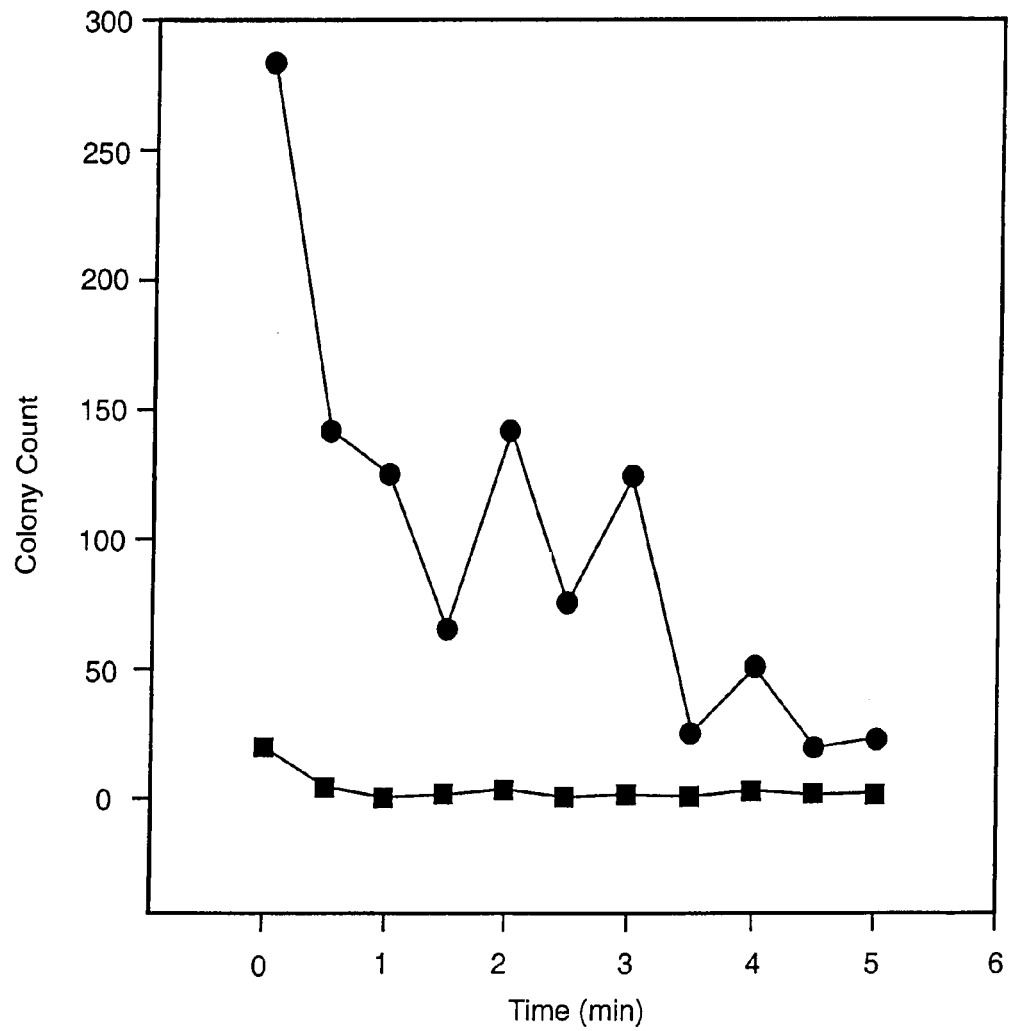
FIG. 1 illustrates the sensitivity of *Bacillus anthracis* (Sterne strain) to heating.

In the inventors' efforts to ascertain the metabolic factors that determine the progress of *Bacillus anthracis* through its life cycle, the inventors have examined various preparations of the special accelerating growth medium 3-amino-L-tyrosine (3AT). This medium has been shown to accelerate germination, growth, and sporulation of *Bacillus anthracis* in preference over other bacilli species. 3AT is described in U.S. Pat. Nos. 5,156,971 and 5,003,050.

Nitration of *Bacillus anthracis* (and other microbes) is believed to cause DNA damage through guanine nitration, depurination and strand breaking. This process can be at least partially repaired in cells that are not killed out right; such repair can lead to mutation. The mutant *Bacillus anthracis* Alls/Gifford (Curlicue) strain appeared in a modified high nitrate-concentration 3AT growth medium. This modified 3AT medium was composed of 55 g of trypticase soy broth (TSB) base, 12 g potassium nitrate, 100 mg luminol (5-amino-2 3-dihydro-1,4-phthalazinedione), and 80 mg 3-amino-L-tyrosine dihydrochloride per liter of water. The medium was inoculated with spores of the Sterne strain of *B. anthracis* derived from the anthrax spore vaccine (Thraxol-2) manufactured by Mobay Corporation. Fifty microliters of the spore suspension were placed in 5 ml of TSB and pre-incubated for 2 hours to allow for germination. Fifty microliters of the germinated suspension were added to 100 ml of the modified 3AT broth medium and allowed to incubate overnight. After 24 hours of growth, the broth cultures were plated onto sheep blood agar and 4×3AT agar plates (4× contains 2× the ingredients of 2×3AT agar). After 48 hours of incubation, small colonies were removed and transferred to blood agar for an additional 24 hours of incubation. Spores were produced from the mutant (small colonies) by taking inoculum from solid media or liquid media and transferring it to blood agar plates and incubating at 37° C. for 4 days. The spores were harvested from the agar plates with wet sterile cotton tipped swabs, which were, in turn, placed in sterile water. Using a sterile funnel, vacuum flask, and filter paper, vacuum collection was made of spores passed through the filter paper in the funnel. The filtrate was centrifuged and the button collected, which contained the pure spores. *Bacillus anthracis* Alls/Gifford strain is currently on deposit at the American Type Culture Collection under the designation PTA-3162.

Applicants have made available to the public without restriction a deposit of *Bacillus anthracis* ag (Alls/Gifford) with the American Type Culture Collection (ATCC), 10801 University Blvd., Manassas, Va. 20110, U.S.A., ATCC Deposit No. PTA-3162. The date of the deposit was the 8th of March, 2001. The deposit with the ATCC was taken from the same deposit maintained by the Air Force, since prior to the filing date of this application. All restrictions imposed by the depositor on the availability to the public of the deposited material will be irrevocably removed upon the granting of the patent. The deposit of the *Bacillus anthracis* ag (Alls/Gifford) without restriction will be maintained at the ATCC Depository, which is a public depository, for a period of 30 years, or five years after the most recent request, or for the effective life of the patent, whichever is longer, and will be replaced if it becomes nonviable during that period.

*Bacillus anthracis* Alls/Gifford has been propagated in culture and its characteristics, phenotypic and genotypic, examined. Upon microscopic examination, the bacteria are long and filamentous initially like other strains of *Bacillus anthracis*, but curl and tightly coil into "knots" when the nutrients in the medium are depleted or the microbe is grown in medium containing bicarbonate or carbon dioxide. Branching is seen unlike other strains of *Bacillus anthracis*. This strain is a slow grower that produces pinpoint colonies on blood agar and 3AT medium. The bacteria does produce viable spores but their production is delayed when compared to other strains. As demonstrated in the following examples, Alls/Gifford, like Sterne, contains the pX01 plasmid, produces luminescent polymer diazoluminomelanin (DALM) when grown in 3AT medium, is penicillin sensitive, is lysed by Cherry gamma phage, is non-hemolytic, and produces nitrite from nitrate. The examples also illustrate that Alls/Gifford does not show growth sensitivity to heat and bicarbonate (carbon dioxide) on 3AT medium, as does Sterne strain, and is less lethal than Sterne.

A genetic fingerprint comparison of the mutant Alls/Gifford with the paternal Sterne strain should reveal the altered genes of the mutant. The protein products of the altered genes found by comparison to Sterne could form the basis for a vaccine that would stimulate antibody to inhibit the bicarbonate/$CO_2$/heat-stimulated growth of anthrax that is necessary for its development in the host. The genes will likely include chromosomal genes that cannot be easily altered by genetic engineering to avoid vaccine protection, without compromising the survivability and pathogenicity of the anthrax. This vaccine could be produced in an expression vector in *E. coli* or become a naked DNA vaccine that no longer requires the whole anthrax or a supernatant derivative to produce. The new vaccine should show decreased side effects and better efficacy in generating an immune response (fewer inoculations). Because germination of spores and growth of the vegetative state should be effected by the antibody induced by the vaccine, it should provide better protection against larger doses of spores than the PA based vaccines.

The following examples illustrate the invention:

Example 1

Genomic DNA Preparation and Polymerase Chain Reaction (PCR)

*Bacillus anthracis* Alls/Gifford (Curlicue) strain was subjected to polymerase chain reaction (PCR) to confirm the presence of the pXO1 plasmid. First, chromosomal DNA was prepared from *Bacillus anthracis* Alls/Gifford as follows. A single colony of *Bacillus anthracis* Alls/Gifford was isolated from a tryptic soy (TSB) agar plate. The colony was used to inoculate 2 ml of TSB, was incubated overnight at 37° C. and next day was used to inoculate 100 ml of TSB, which was incubated for 2 days at 37° C.

The cells were harvested by centrifugation at 8,000 rpm in a Sorvall RC 5B and SS34 rotor at 4° C. The pellet was resuspended in 10 ml 0.32M sucrose, 10 mM Tris HCl pH 7.5, 5 mM $MgCl_2$ solution, and left on ice for 15 min. The suspension was centrifuged as described above. After centrifugation the supernatant was poured off. Resuspension of the pellet was accomplished in 4.5 ml 0.075M NaCl, 0.024M EDTA solution, 0.5 ml 5% SDS and 100 µl Proteinase K (10 mg/ml). The suspension was mixed and left overnight at 37° C. After incubation, 2.5 ml of phenol equilibrated with DNA buffer (10 mM Tris HCl pH 8.0, 1 mM EDTA) was added and the mixture was shaken vigorously, centrifuged briefly, and 2.5 ml chloroform/isoamyl alcohol (24:1 v/v) was added. The mixture was shaken vigorously and centrifuged at 2,500 rpm for 5 min at room temperature. The upper aqueous layer was removed to a clean tube and reextracted with 5.0 ml chloroform/IAA. After shaking, the mixture was centrifuged at 2,500 rpm for 2 min and the top layer remove to a clean tube. To precipitate the DNA 2.2 vol of ice-cold ethanol and ⅒th vol 3M sodium acetate were added and the solution mixed by inversion. The resulting spooled DNA was removed with a sterile tip and dissolved in DNA buffer. The concentration was calculated from reading 1 μl at 260/280 nm with a Spectronic Genesys 5 spectrophotometer.

*Bacillus anthracis* Alls/Gifford DNA (Ba a/g) was diluted to 50 ηg/μl and subjected to polymerase chain reaction (PCR) to confirm that the pXO1 plasmid was still present, and that this was a mutant form of *Bacillus anthracis*. The PCR reaction mix contained 10×PCR buffer (PGC Scientific), 2.6% DMSO, 2 mM dNTPs, 2U Gene Choice TAQ polymerase (PGC Scientific), 200 nM each BAPANTI Forward and BAP-ANTI Reverse2 primers (Genosys) and 5 μl of diluted Ba a/g DNA in a 50 μl reaction volume. The primers were designed to specifically detect the pa antigen gene (pag) carried on the pXO1 plasmid. PCR conditions using a Perkin Elmer 9600 were 96° C. for 2 min, then 94° C. for 1 min, 60° C. for 1 min, 72° C. for 1 min for 35 cycles, followed by 72° C. for 5 min. The size of the PCR product was 959 bp. Using BAPANT Reverse 1 primer a smaller product of 459 bp is formed

| Forward sequence | Reverse sequence | Fragment size |
|---|---|---|
| (SEQ ID NO: 1) atcaccagaggcaag acaccccttgtggc | (SEQ ID NO: 2) R1 tgtaattggagtaga actgaaatcgtcttg | 459 bp |
| | (SEC) ID NO: 3) R2 gctaactgattcttg atattttgagatgtt | 959 bp |

An aliquot of 5 μl from the reaction mixture was subjected to electrophoresis on a 0.8% agarose gel using TAE buffer. Bands were visualized with Ethidium bromide.

Example 2

DALM Synthesis

The Alls/Gifford (Curlicue) strain, like the Sterne strain, synthesizes diazoluminomelanin (DALM). DALM is a luminescent polymer. DALM can be used for chemiluminescent immunoassays for biological and chemical agents; in radiofrequency and ionizing radiation dosimeters; and for RNA/DNA hybridization assays for viruses and genetic detection. DALM is described in U.S. Pat. Nos. 6,013,520, 5,902,728, 5,156,971 and 5,003,050.

To produce DALM, a modified 3AT medium composed of 55 g of trypticase soy broth (TSB) base, 12 g potassium nitrate, 100 mg luminol (5-amino-2 3-dihydro-1,4-phthalazinedione), and 80 mg 3-amino-L-tyrosine dihydrochloride per liter of water was used. The medium was inoculated with spores of the Sterne strain of *B. anthracis* derived from the anthrax spore vaccine (Thraxol-2) manufactured by Mobay Corporation. Fifty microliters of the spore suspension were placed in 5 ml of TSB and pre-incubated for 2 hours to allow for germination. Fifty microliters of the vegetative suspension was added to 100 ml 4×3AT broth and was incubated at 37° C. for 48 hr. The solution was transferred to 15 ml polystyrene screw capped tubes and frozen at −20° C. overnight. The tubes were removed from the freezer and the DALM, which was released from the cells and floated to the top, was removed from the top of the frozen aqueous debris. The presence of DALM in the brown supernatant was confirmed by thermochemiluminescence in a Turner 20E luminometer in a mixture of 100 μL of supernatant, 100 mircroliters of 0.3 M sodium bicarbonate and 100 μL of 0.3% hydrogen peroxide heated to 45° C. Luminescent units produced were compared to a reagent blank containing no supernatant.

Example 3

Sensitivity to Penicillin

The Alls/Gifford (Curlicue) strain, like the Sterne strain, is sensitive to penicillin. Using techniques well known in the art blood plates were spread with a suspension of vegetative *Bacillus anthracis* in TSB and penicillin impregnated disks containing 10U of penicillin were placed on the plate. The plate was incubated at 37° C. and observed. After 5 to 6 hours a clear area was observed extending from the disk showing sensitivity of the *Bacillus anthracis* to the penicillin. Observing the *Bacillus anthracis* cells at the edge of the cleared area microscopically showed the cells to be aligned end to end and rounded in what is described as "string of pearls" formation. This observation is one of the definitive tests for the presence of *Bacillus anthracis*.

Example 4

Cherry Gamma Phage

The Alls/Gifford (Curlicue) strain, like the Sterne strain, is lysed by the Cherry gamma phage. Using techniques well known in the art blood agar plates were spread with a suspension of *Bacillus anthracis* vegetative cells in TSB and the plate incubated at 37° C. for 3 to 4 hour. A suspension was made and 100, 50, 20, and 10 μl, aliquots were dropped on to the lawn of *Bacillus anthracis*. The plates were incubated overnight and observed. Clear areas could be seen in the bacterial lawn where the Cherry gamma phage suspension had been applied. By reducing the volume applied the titer of the phage suspension could be determined. This test is definitive for the presence of *Bacillus anthracis*.

Example 5

Non-Hemolytic

The Alls/Gifford (Curlicue) strain, like the Sterne strain, is non-hemolytic. Using techniques well known in the art a suspension of the Alls/Gifford strain in TSB was spread on a blood agar plate and incubated at 37° C. overnight. The blood plate showed growth of the bacteria, but no haemolysis of the blood was observed Example 6

Production of Nitrite from Nitrate

The Alls/Gifford (Curlicue) strain, like the Sterne strain, produces nitrite from nitrate. Cells were grown in 2.0 ml TSB overnight. Fifty microliters of this suspension were added to 2.0 ml of 4×3AT medium and allowed to incubate overnight at 37° C. The suspension was spun to pellet the cells, the 50 μL of the supernatant removed to a clean tube and 50 μL of Griess reagent A and 50 μL of Griess reagent B were added. A pink color was observed indicating the presence of nitrite.

Example 7

Thermal Sensitivity

The thermal sensitivities of Sterne and Alls/Gifford were compared. First, single-spore suspensions of Sterne were prepared as follows: The Sterne spore vaccine was centrifuged, the supernatant decanted, and the pellet washed with chilled deionized water. Dilute powdered milk solution was made with chilled deionized water to a concentration of 26 mg of milk solids per ml of sterile milk solution. Fifty microliters of this suspension were diluted with 450 μL of physiological phosphate buffered saline (PBS) and used as the source of colony forming unit (CFU) assays. Three microliters of the well suspended spore/skim milk suspension were transferred to the tip of a siliconized sterile pipet. The suspension was frozen and lyophilized for four to five days. The pipettes, charged with spores, were stored under vacuum at room temperature when not needed.

Single-spore suspensions of Alls/Gifford were prepared as follows: Fifty microliters of *Bacillus anthracis* Spore Vaccine, Thraxol-2, manufactured by Mobay Corporation was grown in 5.0 ml of TSB and pre-incubated for 2 hours (to allow for germination). Fifty microliters of the germinated suspension was added to 100 ml of 3AT medium containing 55 g TSB, 12 g Potassium nitrate, 100 mg Luminol, 80 mg 3AT per liter and allowed to incubate overnight. After 24 hour of growth the broth was plated to blood agar plates and 4×3AT solid medium. Small colonies were harvested from the plates after 24 hr and replated on blood agar plates. Colonies were allowed to grow on blood agar plates for 48 hours when they were harvested into 4×3AT medium and spun. The pellet was washed in chilled deionized water, spun and resuspended in powdered dry milk solution (26 mg/ml). Fifty microliters of this suspension were diluted with 450 μL of physiological phosphate buffered saline (PBS) and used as the source of colony forming units (CFUs) for the assays. Three microliters of the well-suspended spore/skim milk suspension were transferred to the tip of a siliconized sterile pipet. The suspension was frozen and lyophilized for four to five days. The pipettes, charged with spores, were stored under vacuum at room temperature when not needed.

The lyophilized Sterne and Alls/Gifford spore samples were heated for 1 second at various temperatures by placing them in the heating block of the melting point apparatus, which had been preheated to the desired temperatures. The pipettes were washed with 450 μL of sterile PBS. The spores were plated on either blood or 4×3AT agar for 24 hours. A plate received either 1 μL of the recovered spores by using a calibrated loop or 50 μL of the suspension. The plates were incubated overnight at 37° C. and counted the next day for colonies. In FIG. 1, the sensitivity of Sterne to heating is demonstrated. Starting at about 180° C. on blood agar (indicated by circles), Sterne is affected by its exposure to heat. At 275° C., a 1 second exposure has killed all the Sterne spores. Sterne grown on 4×3AT media (as indicated by squares) is less viable than that grown on blood agar because the 4×3AT media is more stringent toward the growth of *Bacillus anthracis*. Sterne on 3AT is affected by heat starting at about 130° C. Sterne is no longer viable after a 1 second exposure at 280° C.

Figure 2:
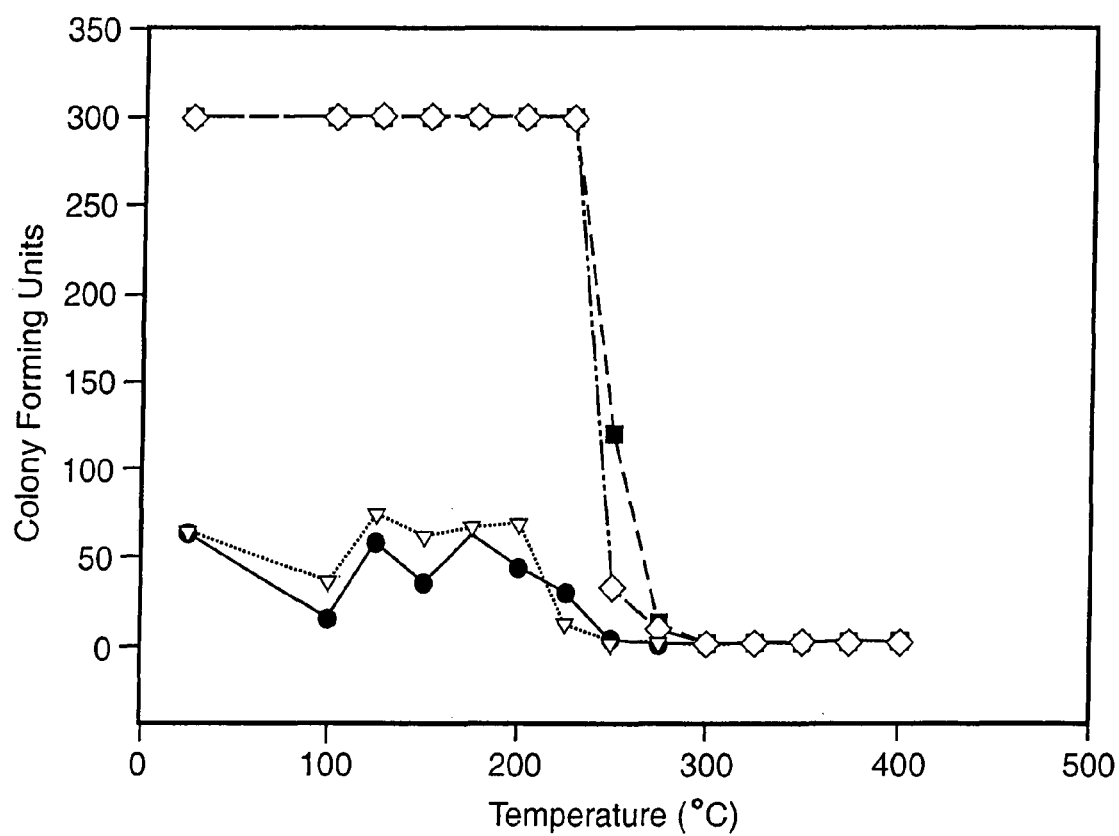
FIG. 2 illustrates the sensitivity of the Alls/Gifford (Curlicue) strain to heating.

The thermal resistance of Alls/Gifford is demonstrated in FIG. 2. Starting at about 40° C., on blood agar, Alls/Gifford is affected by its exposure to heat (1 μL of inoculum on blood agar, as indicated by circles). Fifty microliters of Alls/Gifford grown on 4×3AT media (as indicated by diamonds) is affected by heat starting at about 240° C. Results for 1 μL of inoculum on 4×3AT media (as indicated by triangles) and 50 μL of inoculum on blood agar (as indicated by squares) are also illustrated. At 300° C., a 1 second exposure has killed all of the Alls/Gifford spores on both media. Comparison of FIGS. 1 and 2 indicate the increased sensitivity of Sterne to heat, and relative thermal resistance of Alls/Gifford. To further confirm the thermal resistance of Alls/Gifford, using techniques well known in the art, attempts were made to cure Alls/Gifford of its pX01 plasmid by 10 passages and cultivation over many days at 42° C. These attempts failed. By contrast, when Sterne strain is grown at an elevated temperature (42° C.) for ten days and passaged to new medium every 24 hours, Sterne is cured of its pX01 plasmid.

Figure 3:
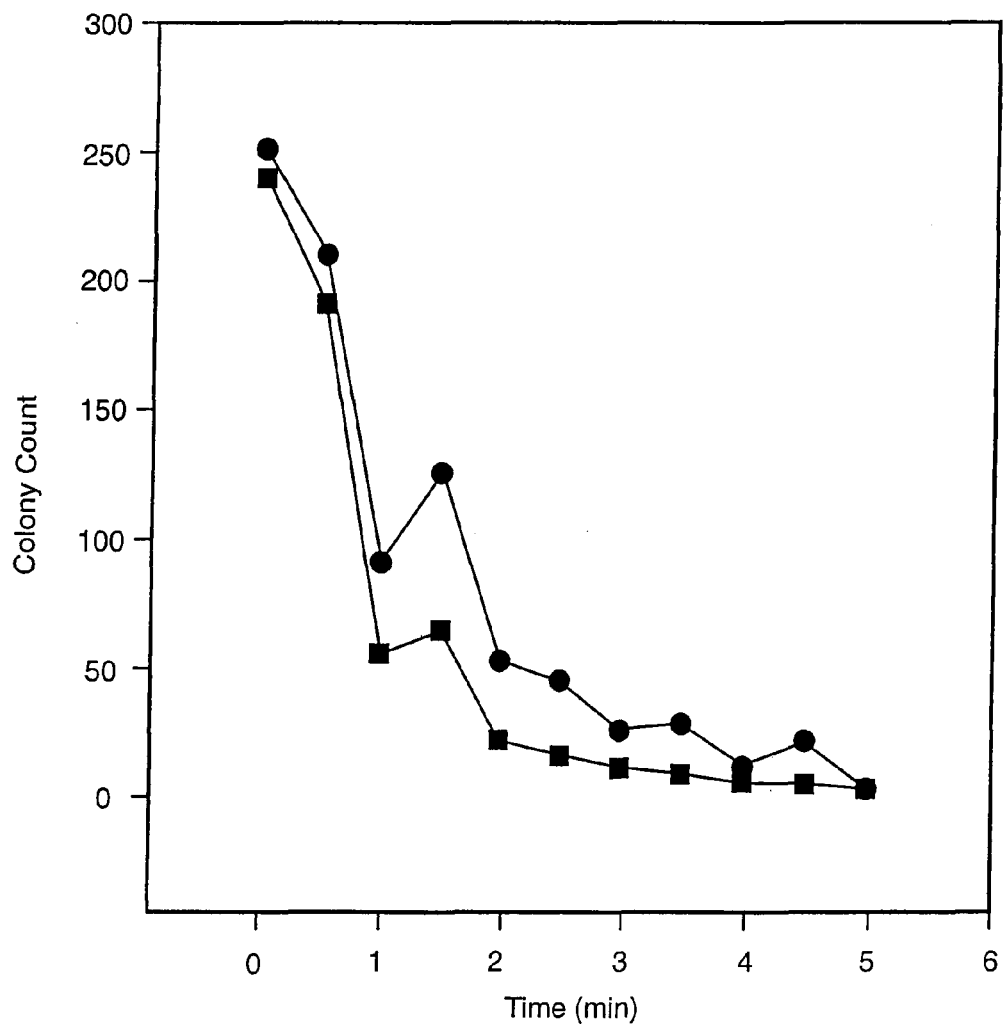
FIG. 3 illustrates the thermal response of Sterne strain at 125° C. on blood agar and 4×3XAT media in the absence of $CO_2$.
Figure 4:
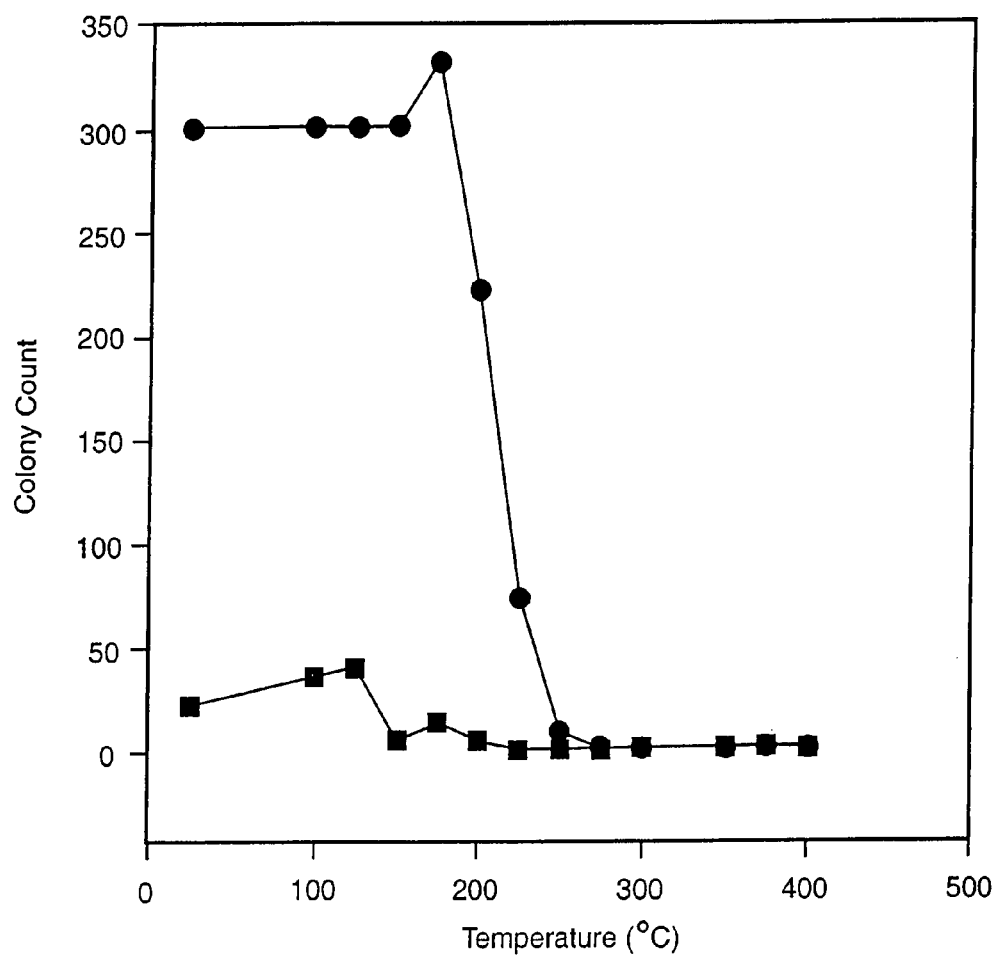
FIG. 4 illustrates the thermal response of Sterne strain at 125° C. on blood agar and 4×3XAT media in the presence of $CO_2$.

FIGS. 3 and 4 demonstrate the alteration of the thermal sensitivity of Sterne strain with CO2 or bicarbonate on 4×3AT media. The thermal sensitivity of Alls/Gifford (Curlicue) strain, however, was not altered by addition of CO2 or bicarbonate under the same conditions. Carbon dioxide was added to growth conditions using techniques well known in the art ($CO_2$ gas generator placed in a zip-lock bag with the culture medium plates during incubation). Dry spores of Sterne strain and Alls/Gifford (Curlicue) strain were exposed to 125° C. for various lengths of time. FIG. 3 illustrates the thermal response of Sterne strain on blood agar (as indicated by circles) and on 4×3AT media (as indicated by squares) without CO2. FIG. 4 illustrates the thermal response of Sterne strain on blood agar (as indicated by circles) and on 4×3AT media (as indicated by squares) with CO2. FIGS. 3 and 4 show that thermal sensitivity of Sterne on 4×3AT media was altered by the presence of carbon dioxide. Alls/Gifford (Curlicue) strain, however, did not display this difference in thermal sensitivity.

Example 8

Bicarbonate/CO2 Control

Bicarbonate/CO2 control over growth response was further examined as follows. Alls/Gifford strain was grown in 3AT medium with and without bicarbonate and the results compared with growth of Sterne strain under the same conditions. First, a suspension of spores of each *bacillus* strain was prepared in phosphate buffered saline (PBS; pH 7.4). To determine the initial colony forming units, each was diluted 10-fold to a $1:10^6$ dilution by transferring 50 μL of suspension into 4504 of PBS. A 1-μL calibrated loop was used to streak sheep blood agar or 4×3AT agar (4× contains 2× the ingredients of 2×3AT agar). Fifty milliliters of TSB, 2×3AT, or 2×3AT with bicarbonate (2 g/l sodium bicarbonate) were each placed in a 250-ml flask. Each was inoculated with 50 μL of the 1:10 dilution of the respective *bacillus*. The flasks were incubated in a shaker incubator at 37° C. Phase contrast microscopic examination of colonies performed after 24 hours in liquid medium, indicated that bicarbonate accelerates spore formation in Sterne, but not in Alls/Gifford.

Example 9

Lethality

Figure 5:
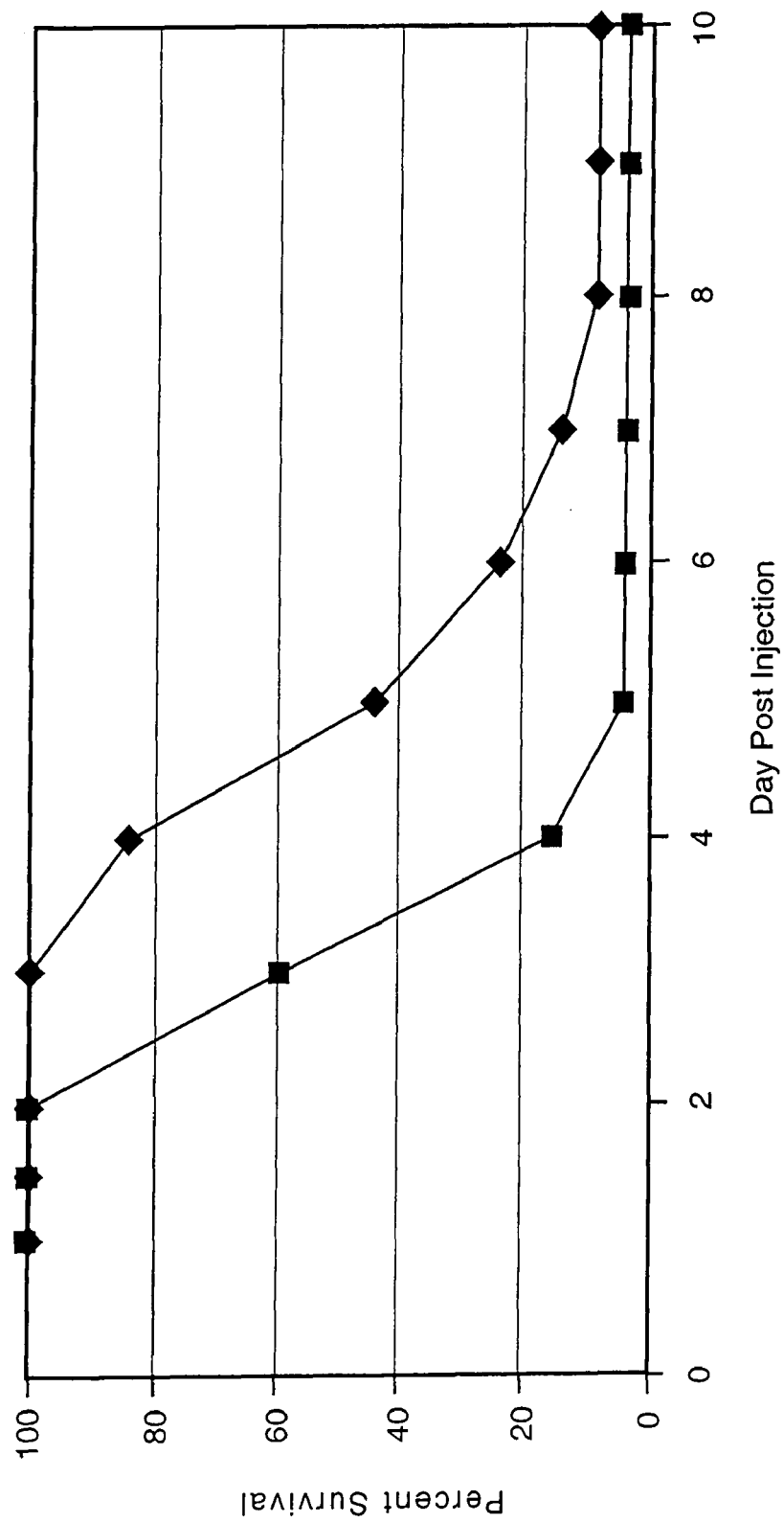
FIG. 5 illustrates time to death (TTD) of laboratory mice following infection with Sterne strain and Alls/Gifford (Curlicue) strain.

A study was conducted comparing response of laboratory mice to infection with Alls/Gifford (Curlicue) strain compared to the Sterne strain. Mice were injected subcutaneously with spore (one group with Sterne spores and another with Alls/Gifford (Curlicue) spores). Results show that Alls/Gifford strain kills mice at the same high dose as Sterne strain ($1 \times 10^6$), but at a much delayed rate; Alls/Gifford starts killing approximately 24 hours later than Sterne. This result is illustrated in FIG. 5. The squares represent Sterne-infected mice; diamonds, Alls/Gifford-infected mice. TTD (time to death) is shown to be later following infection with Alls/Gifford strain.

We claim:

1. A composition comprising:
   about 55 g of trypticase soy broth (TSB) base;
   about 12 g potassium nitrate;
   about 100 mg luminol (5-amino-2 3-dihydro-1; 4-phthalazinedione); and
   about 80 mg 3-amino-L-tyrosine dihydrochloride per liter of water.

2. A method comprising:
   providing as a medium the composition of claim 1; and
   inoculating said medium with a paternal bacteria strain;
   whereby a mutated bacteria strain is produced.

3. The method of claim 2 wherein said paternal bacteria strain is *Bacillus anthracis*.

4. The method of claim 3 further comprising:
   introducing cells of said mutated bacteria strain into a laboratory animal; and
   producing delayed onset of death in said laboratory animal, compared to an animal into which said paternal bacteria strain is introduced.

5. The method of claim 2 wherein said paternal bacteria strain is the Sterne strain of *Bacillus anthracis*.

6. A method comprising:
   culturing in a medium a cell of the mutated strain of claim 2, under conditions permitting expression of protein products; and
   purifying one or more of said protein products from said cell or medium of said cell.

* * * * *